(12) United States Patent
Rosier et al.

(10) Patent No.: US 7,612,223 B2
(45) Date of Patent: Nov. 3, 2009

(54) PROCESS FOR THE HYDROCYANATION OF UNSATURATED COMPOUNDS

(75) Inventors: Cécile Rosier, Soucieu en Jarrest (FR); Philippe Leconte, Meyzieu (FR); Damien Bourgeois, Lyons (FR)

(73) Assignee: Invista North America S.A R.L., Wilmington, DE (US)

( * ) Notice: Subject to any disclaimer, the term of this patent is extended or adjusted under 35 U.S.C. 154(b) by 220 days.

(21) Appl. No.: 10/556,628

(22) PCT Filed: May 7, 2004

(86) PCT No.: PCT/FR2004/001110

§ 371 (c)(1), (2), (4) Date: Sep. 21, 2006

(87) PCT Pub. No.: WO2004/101498

PCT Pub. Date: Nov. 25, 2004

(65) Prior Publication Data

US 2007/0155979 A1 Jul. 5, 2007

(30) Foreign Application Priority Data

May 12, 2003 (FR) .................................. 03 05673

(51) Int. Cl.
 *C07C 253/00* (2006.01)
(52) U.S. Cl. .......................... 558/335; 558/332; 556/14
(58) Field of Classification Search ................. 558/335, 558/332; 556/14
 See application file for complete search history.

(56) References Cited

U.S. PATENT DOCUMENTS

| | | | |
|---|---|---|---|
| 2,402,873 A | 6/1946 | Coffman et al |
| 2,570,199 A | 10/1951 | Brown |
| 2,583,984 A | 1/1952 | Arthur, Jr. |
| 2,666,780 A | 1/1954 | Arthur, Jr. |
| 3,282,981 A | 11/1966 | Davis |
| 3,297,742 A | 1/1967 | Monroe, Jr. |
| 3,328,443 A | 6/1967 | Clark |
| 3,340,207 A | 9/1967 | Baker |
| 3,496,210 A | 2/1970 | Drinkard, Jr. |
| 3,496,215 A | 2/1970 | Drinkard, Jr. |
| 3,496,217 A | 2/1970 | Drinkard, Jr. |
| 3,496,218 A | 2/1970 | Drinkard, Jr. |
| 3,522,288 A | 7/1970 | Drinkard, Jr. |
| 3,526,654 A | 9/1970 | Hildebrand |
| 3,536,748 A | 10/1970 | Drinkard, Jr. |
| 3,538,142 A | 11/1970 | Drinkard, Jr. |
| 3,542,847 A | 11/1970 | Drinkard, Jr. |
| 3,547,972 A | 12/1970 | Drinkard, Jr. |
| 3,551,474 A | 12/1970 | Drinkard, Jr. |
| 3,563,698 A | 2/1971 | Rushmere |
| 3,564,040 A | 2/1971 | Downing |
| 3,579,560 A | 5/1971 | Drinkard, Jr. |
| 3,631,191 A | 12/1971 | Kane |
| 3,641,107 A | 2/1972 | Breda |
| 3,651,146 A | 3/1972 | Schriltz |
| 3,652,641 A | 3/1972 | Druliner |
| 3,655,723 A | 4/1972 | Drinkard, Jr. |
| 3,676,475 A | 7/1972 | Drinkard, Jr. |
| 3,676,481 A | 7/1972 | Chia |
| 3,694,485 A | 9/1972 | Drinkard, Jr. |
| 3,739,011 A | 6/1973 | Drinkard |
| 3,752,839 A | 8/1973 | Drinkard |
| 3,766,231 A | 10/1973 | Wayne |
| 3,766,237 A | 10/1973 | Squire |
| 3,766,241 A | 10/1973 | Drinkard |
| 3,773,809 A | 11/1973 | Walter et al. |
| 3,775,461 A | 11/1973 | Drinkard |
| 3,798,256 A | 3/1974 | King |
| 3,818,067 A | 6/1974 | Downing |
| 3,818,068 A | 6/1974 | Wells |
| 3,846,461 A | 11/1974 | Shook |
| 3,846,474 A | 11/1974 | Mok |
| 3,847,959 A | 11/1974 | Shook |
| 3,850,973 A | 11/1974 | Seidel |
| 3,852,325 A | 12/1974 | King |
| 3,852,327 A | 12/1974 | Druliner |
| 3,852,328 A | 12/1974 | Chia |
| 3,852,329 A | 12/1974 | Tomlinson |

FOREIGN PATENT DOCUMENTS

WO   WO 03/011457 A   2/2003

OTHER PUBLICATIONS

Kreutzer et al., 1996, CAS: 125:114851.*
International Search Report dated Dec. 2, 2004 for PCT/FR2004/00110.

* cited by examiner

Primary Examiner—Rei-tsang Shiao

(57) ABSTRACT

The present invention relates to a process for the hydrocyanation of unsaturated compounds to unsaturated mononitrile compounds or to dinitrile compounds; It relates more particularly to a process for the manufacture of dinitriles by double hydrocyanation of diolefins, such as butadiene, comprising a recovery and separation of the catalytic system. The process for the manufacture of dinitriles of the invention by hydrocyanation of unsaturated compounds, comprising at least one stage of hydrocyanation in the presence of a catalytic system comprising an organometallic complex formed by one or more monodentate organophosphite ligands and one or more bidentate organophosphorus ligands and optionally a promoter of Lewis acid type, comprises at least one stage of separation by distillation of a reactant used in the process or of a compound formed by the reaction from a medium comprising the said catalytic system.

11 Claims, No Drawings

U.S. PATENT DOCUMENTS

| | | |
|---|---|---|
| 3,853,754 A | 12/1974 | Gosser |
| 3,853,948 A | 12/1974 | Drinkard |
| 3,859,327 A | 1/1975 | Wells |
| 3,864,380 A | 2/1975 | King |
| 3,865,865 A | 2/1975 | Musser |
| 3,884,997 A | 5/1975 | Shook, Jr. |
| 3,903,120 A | 9/1975 | Shook, Jr. |
| 3,920,721 A | 11/1975 | Gosser |
| 3,925,445 A | 12/1975 | King |
| 3,927,056 A | 12/1975 | Gosser |
| 3,983,011 A | 9/1976 | Wiggill |
| 3,997,579 A | 12/1976 | Jesson |
| 4,045,495 A | 8/1977 | Nazarenko |
| 4,046,815 A | 9/1977 | Nazarenko |
| 4,076,756 A | 2/1978 | Nazarenko |
| 4,080,374 A | 3/1978 | Corn |
| 4,082,811 A | 4/1978 | Shook, Jr. |
| 4,134,923 A | 1/1979 | Reimer |
| 4,146,555 A | 3/1979 | Kershaw |
| 4,147,717 A | 4/1979 | Kershaw |
| 4,177,215 A | 12/1979 | Seidel |
| 4,251,468 A | 2/1981 | Nazarenko |
| 4,298,546 A | 11/1981 | McGill |
| 4,328,172 A | 5/1982 | Rapoport |
| 4,330,483 A | 5/1982 | Rapoport |
| 4,336,110 A | 6/1982 | Reimer |
| 4,339,395 A | 7/1982 | Barnette |
| 4,347,193 A | 8/1982 | Shook, Jr. |
| 4,371,474 A | 2/1983 | Rapoport |
| 4,382,038 A | 5/1983 | McGill |
| 4,385,007 A | 5/1983 | Shook, Jr. |
| 4,387,056 A | 6/1983 | Stowe |
| 4,394,321 A | 7/1983 | Cone |
| 4,416,824 A | 11/1983 | Reimer |
| 4,416,825 A | 11/1983 | Ostermaier |
| 4,434,316 A | 2/1984 | Barnette |
| 4,510,327 A | 4/1985 | Peet |
| 4,521,628 A | 6/1985 | Ostermaier |
| 4,539,302 A | 9/1985 | Leyendecker et al. |
| 4,705,881 A | 11/1987 | Rapoport |
| 4,714,773 A | 12/1987 | Rapoport |
| 4,749,801 A | 6/1988 | Beatty |
| 4,774,353 A | 9/1988 | Hall |
| 4,783,546 A | 11/1988 | Burke |
| 4,810,815 A | 3/1989 | Bryndza |
| 4,874,884 A | 10/1989 | McKinney |
| 4,990,645 A | 2/1991 | Back |
| 5,087,723 A | 2/1992 | McKinney |
| 5,107,012 A | 4/1992 | Grunewald |
| 5,143,873 A | 9/1992 | Bryndza |
| 5,175,335 A | 12/1992 | Casalnuovo |
| 5,312,957 A | 5/1994 | Casalnuovo |
| 5,312,959 A | 5/1994 | Sieja |
| 5,382,697 A | 1/1995 | Casalnuovo |
| 5,440,067 A | 8/1995 | Druliner |
| 5,449,807 A | 9/1995 | Druliner |
| 5,484,902 A | 1/1996 | Casalnuovo |
| 5,510,470 A | 4/1996 | Casalnuovo |
| 5,512,695 A | 4/1996 | Kreutzer |
| 5,512,696 A | 4/1996 | Kreutzer |
| 5,523,453 A | 6/1996 | Breikss |
| 5,543,536 A | 8/1996 | Tam |
| 5,663,369 A | 9/1997 | Kreutzer |
| 5,688,986 A | 11/1997 | Tam |
| 5,693,843 A | 12/1997 | Breikss |
| 5,696,280 A | 12/1997 | Shapiro |
| 5,709,841 A | 1/1998 | Reimer |
| 5,723,641 A | 3/1998 | Tam |
| 5,821,378 A | 10/1998 | Foo |
| 5,847,191 A | 12/1998 | Bunel |
| 5,959,135 A | 9/1999 | Garner |
| 5,981,772 A | 11/1999 | Foo |
| 6,020,516 A | 2/2000 | Foo |
| 6,031,120 A | 2/2000 | Tam |
| 6,048,996 A | 4/2000 | Clarkson |
| 6,069,267 A | 5/2000 | Tam |
| 6,077,979 A | 6/2000 | Qiu |
| 6,120,700 A | 9/2000 | Foo |
| 6,121,184 A | 9/2000 | Druliner |
| 6,127,567 A | 10/2000 | Garner |
| 6,171,996 B1 | 1/2001 | Garner |
| 6,171,997 B1 | 1/2001 | Foo |
| 6,284,865 B1 | 9/2001 | Tam |
| 6,362,354 B1 | 3/2002 | Bunel |
| 6,372,147 B1 | 4/2002 | Reimer |
| 6,380,421 B1 | 4/2002 | Lu |
| 6,399,534 B2 | 6/2002 | Bunel |
| 6,420,611 B1 | 7/2002 | Tam |
| 6,461,481 B1 | 10/2002 | Barnette |
| 6,489,517 B1 | 12/2002 | Shapiro |
| 6,555,718 B1 | 4/2003 | Shapiro |
| 6,646,148 B1 | 11/2003 | Kreutzer |
| 6,660,876 B2 | 12/2003 | Gagne |
| 6,660,877 B2 | 12/2003 | Lenges |
| 6,737,539 B2 | 5/2004 | Lenges |
| 6,753,440 B2 | 6/2004 | Druliner |
| 6,812,352 B2 | 11/2004 | Kreutzer |
| 6,844,289 B2 | 1/2005 | Jackson |
| 6,846,945 B2 | 1/2005 | Lenges |
| 6,855,799 B2 | 2/2005 | Tam |
| 6,893,996 B2 | 5/2005 | Chu |
| 6,897,329 B2 | 5/2005 | Jackson |
| 6,906,218 B2 | 6/2005 | Allgeier |
| 6,924,345 B2 | 8/2005 | Gagne |
| 6,936,171 B2 | 8/2005 | Jackson |
| 6,984,604 B2 | 1/2006 | Cobb |
| 7,071,365 B2 | 7/2006 | Lu |
| 7,084,293 B2 * | 8/2006 | Rosier et al. ............... 558/335 |
| 7,345,006 B2 | 3/2008 | Bartsch et al. |
| 2003/0100802 A1 | 5/2003 | Shapiro |
| 2004/0106815 A1 | 6/2004 | Ritter |
| 2005/0059737 A1 | 3/2005 | Allgeier |
| 2005/0159614 A1 | 7/2005 | Allgeier |
| 2007/0219386 A1 | 9/2007 | Ritter |
| 2008/0015378 A1 | 1/2008 | Foo |
| 2008/0015379 A1 | 1/2008 | Garner |
| 2008/0015380 A1 | 1/2008 | Foo |
| 2008/0015381 A1 | 1/2008 | Foo |
| 2008/0015382 A1 | 1/2008 | Foo |

PROCESS FOR THE HYDROCYANATION OF UNSATURATED COMPOUNDS

This application is an application under 35 U.S.C. Section 371 of International Application Number PCT/FR2004/001110 filed on May 7, 2004.

The present invention relates to a process for the hydrocyanation of unsaturated compounds to unsaturated mononitrile compounds or to dinitrile compounds.

It relates more particularly to a process for the manufacture of dinitriles by double hydrocyanation of diolefins, such as butadiene, comprising a recovery and separation of the catalyst system.

The hydrocyanation reaction is used industrially for the synthesis of compounds comprising nitrile functional groups from compounds comprising unsaturations. Thus, adiponitrile, which is an important chemical intermediate, in particular in the manufacture of hexamethylene diamine, a monomer for a number of polymers, such as polyamide, is manufactured by hydrocyanation in two stages of butadiene or of a hydrocarbon cut, known as C4 cut, comprising butadiene. In this manufacturing process, the two reactions are carried out with catalytic systems comprising essentially the same entities, namely an organometallic coordination complex and at least one organophosphorus ligand of monodentate organophosphite type, such as tritolyl phosphite.

Numerous patents disclose this process for the manufacture of adiponitrile and processes for the manufacture of the catalysts.

Furthermore, for the economics of the process, it is important to be able to recover the catalytic system and to recycle it in the hydrocyanation stages.

Thus, U.S. Pat. No. 4,539,302 discloses a process for the recovery of the catalyst from the reaction medium obtained in the second stage of the process for the preparation of adiponitrile, namely the hydrocyanation of unsaturated nitriles to dinitriles.

This process for recovery by settling makes it possible to limit the losses of metal element and facilitates the control of the organophosphorus ligand/metal element ratio for the hydrocyanation of unsaturated nitriles. Thus, it is also possible to recover a catalytic system with a high ligand/metal element ratio which makes possible recycling and reuse of the catalytic system in the stages for the manufacture of catalyst and/or in the stages of hydrocyanation of butadiene or the isomerization of branched pentenenitriles.

Numerous other organophosphorus ligands have been provided for the catalysis of these hydrocyanation reactions.

Thus, bidentate ligands of organophosphite, organophosphinite, organophosphonite and organophosphine type have been disclosed in numerous patents, such as, for example, Patents WO 99/06355, WO 99/06356, WO 99/06357, WO 99/06358, WO 99/52632, WO 99/65506, WO 99/62855, U.S. Pat. No. 5,693,843, WO 96/1182, WO 96/22968, U.S. Pat. No. 5,981,772, WO 01/36429, WO 99/64155 or WO 02/13964.

Finally, provision has also been made, in patent WO 03/11457, to use a mixture of mono- and bidentate ligands for the catalysis of hydrocyanation reactions.

In the case of mixtures of ligands, it is also important to be able to recover the catalyst without losing ligands or metal element.

One of the aims of the present invention is to provide a process for the manufacture of dinitriles by hydrocyanation of unsaturated compounds using a catalytic system comprising a mixture of monodentate organophosphite ligands and of bidentate organophosphorus ligands which makes possible separation and recovery of the catalyst and of various products with minimum loss of compounds forming the catalytic system.

To this end, the invention provides a process for the manufacture of dinitriles by hydrocyanation of unsaturated compounds comprising at least one stage of hydrocyanation in the presence of a catalytic system comprising an organometallic complex formed by one or more organophosphorus ligands of monodentate organophosphite type and one or more bidentate organophosphorus ligands and optionally a promoter of Lewis acid type and at least one stage of separation by distillation of a reactant used in the process or of a compound formed by the reaction from a medium comprising the said catalytic system, characterized in that the medium subjected to the stage of separation by distillation comprises a ratio of the number of moles of monodentate and bidentate organophosphorus ligands, expressed as phosphorus atoms, with respect to the number of metal element atoms of less than or equal to 15 and/or a concentration by weight of metal element forming the organometallic complex of less than or equal to 1.3%, and in that the distillation bottom temperature of the distillation stage is less than or equal to 180° C.

The term "distillation bottom temperature" is understood to mean the temperature of the medium present in the boiler of the distillation plant and the temperature of the walls of the boiler.

The distillation conditions and in particular the maximum temperature of the walls of the boiler make it possible to limit and even to eliminate the precipitation of the metal element forming the organometallic complex. This is because a higher temperature can bring about decomplexing of the catalyst, resulting in the precipitation of the metal element, during the separation or distillation stage.

The metal elements exhibiting a catalytic effect in a hydrocyanation reaction are, for example, nickel, cobalt, iron, ruthenium, rhodium, palladium, osmium, iridium, platinum, copper, silver, gold, zinc, cadmium or cerium. Nickel is the preferred catalytic element. For greater clarity, the metal element will be denoted by the term "nickel" in the continuation of the present text, without this having a limiting meaning.

Mention may be made, as monodentate organophosphite ligands which are suitable for the invention, by way of examples, of triphenyl phosphite, tritolyl phosphite (TTP) or tricymenyl phosphite.

Mention may be made, as bidentate ligands which are suitable for the invention, of organophosphite, organophosphonite, organophosphinite or organophosphine compounds and in particular of those with the following structures, in which Ph means phenyl:

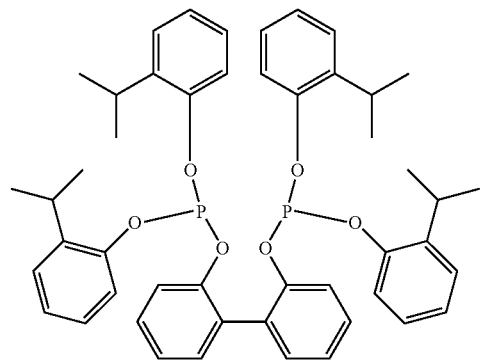

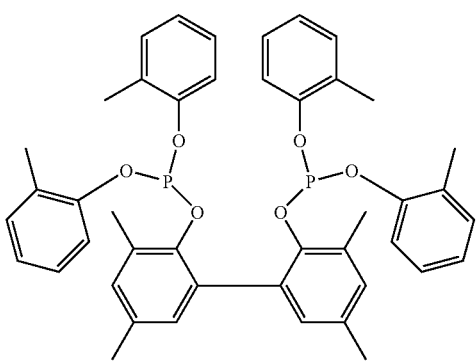

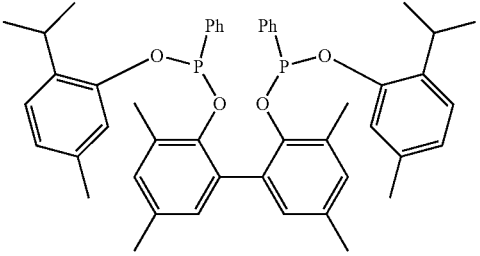

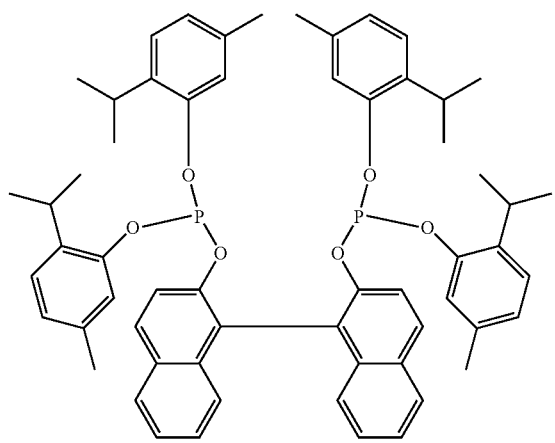

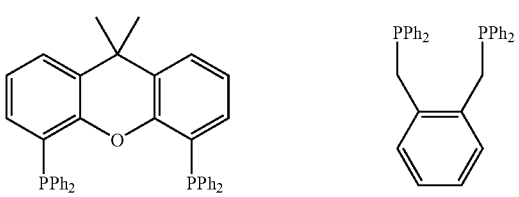

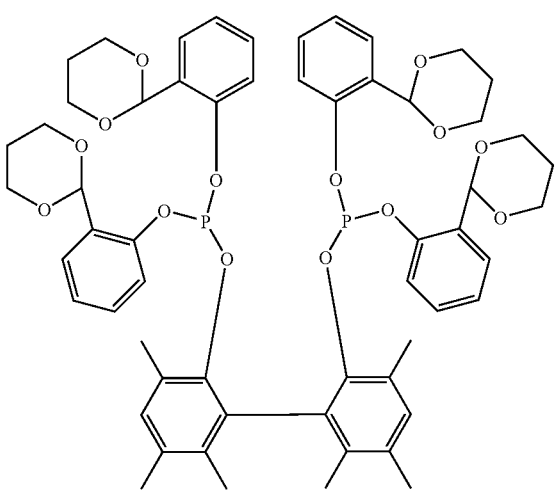

According to a preferred characteristic of the invention, the catalytic system present in the reaction medium generally comprises a number of moles of bidentate ligands, expressed as the number of phosphorus atoms with respect to a metal element atom, of between 1 and 4 (limits included), while that of monodentate ligands, expressed as the number of phosphorus atoms, is between 4 and 12 (limits included).

These ratios can be different according to the hydrocyanation reaction carried out. This is because the manufacture of dinitriles is generally carried out in two successive stages consisting, in a first stage, in hydrocyanating a diolefin, such as butadiene, with HCN to give unsaturated mononitriles and, in a second stage, in converting these mononitriles to dinitriles by reaction with HCN. Furthermore, the process generally comprises a stage of isomerization of the branched unsaturated mononitriles obtained from the first stage in order to convert them to linear mononitriles which will be converted to linear dinitriles in the second stage.

Thus, the ligand/nickel ratio used in the first stage is generally higher than that used in the second stage. Likewise, the concentration of nickel can be different in the two stages.

Furthermore, in the reaction for the hydrocyanation of the unsaturated nitriles or second stage, a promoter or cocatalyst is generally used. Lewis acids are generally chosen as preferred promoters.

Use may in particular be made, by way of examples, of the Lewis acids mentioned in the work edited by G. A. Olah "Friedel-Crafts and Related Reactions", volume I, pages 191 to 197 (1963).

The Lewis acids which can be employed as cocatalysts in the present process are advantageously chosen from compounds of the elements from Groups Ib, IIb, IIIa, IIIb, IVa, IVb, Va, Vb, VIIb, VIIb and VIII of the Periodic Table of the Elements. These compounds are generally salts, in particular halides, such as chlorides or bromides, sulphates, sulphonates, haloalkylsulphonates, perhaloalkylsulphonates, in particular fluoroalkylsulphonates or perfluoroalkylsulphonates, haloacetates, perhaloacetates, carboxylates and phosphates.

Mention may be made, as nonlimiting examples of such Lewis acids, of zinc chloride, zinc bromide, zinc iodide, manganese chloride, manganese bromide, cadmium chloride, cadmium bromide, stannous chloride, stannous bromide, stannous sulphate, stannous tartrate, indium chloride, indium trifluoromethylsulphonate, indium trifluoroacetate, chlorides or bromides of rare earth elements, such as lanthanum, cerium, praseodymium, neodymium, samarium, europium, gadolinium, terbium, dysprosium, hafnium, erbium, thulium, ytterbium and lutetium, cobalt chloride, ferrous chloride or yttrium chloride.

Use may also be made, as Lewis acid, of compounds such as triphenylborane or titanium tetraisopropoxide.

It is, of course, possible to employ mixtures of several Lewis acids.

Preference is very particularly given, among Lewis acids, to zinc chloride, zinc bromide, stannous chloride, stannous bromide, triphenylborane, indium trifluoromethylsulphonate, indium trifluoroacetate and zinc chloride/stannous chloride mixtures.

The Lewis acid cocatalyst employed generally represents from 0.005 to 50 mol per mole of nickel.

In each of these stages, the reaction medium obtained after the hydrocyanation reaction is advantageously subjected to separation by distillation of the unreacted reactant, namely butadiene or the unsaturated nitrile, in order to be recycled.

According to invention, these separation stages are carried out while observing a distillation bottom temperature according to the conditions of ligand/nickel ratio and nickel concentration indicated above in order to avoid or limit decomplexing of the nickel and its precipitation.

According to preferred characteristics of the invention, the total ligand/nickel ratio, expressed as number of phosphorus atoms with respect to the number of nickel atoms, is preferably less than or equal to 15, advantageously between 5 and 15, the concentration by weight of nickel advantageously being between 0.1% and 2%, preferably between 0.1% and 1.2% (limits included).

The term "total ligand" is understood to mean all the molecules of monodentate and bidentate ligands. In the present text, the expression "ligand/nickel" also relates to the ratio of all the molecules of mono- and bidentate ligands with respect to the number of nickel atoms, unless expressly indicated otherwise.

Thus, in the case of the separation of butadiene or C4 petroleum cut by distillation of the reaction medium resulting from the first hydrocyanation stage, the maximum temperature of the distillation bottoms is less than or equal to 180° C. for a ratio of moles of bidentate ligand, expressed as phosphorus atoms, to the number of nickel atoms of between 1 and 4 (limits included) and that of the monodentate ligand of between 4 and 12 (limits included). In addition, according to a preferred characteristic of the invention, the concentration by weight of nickel is greater than or equal to 0.1%, advantageously greater than 0.2%.

Likewise, in the stage of separation of the unsaturated nitrites from the medium resulting from the second stage of hydrocyanation of the unsaturated nitrites, the distillation bottom temperature is advantageously less than or equal to 140° C. for a ratio of moles of bidentate ligand, expressed as phosphorus atoms, to the number of nickel atoms of between 1 and 4 (limits included) and that of the monodendate ligand of between 4 and 7 (limits included). In addition, according to a preferred characteristic of the invention, the concentration by weight of nickel is greater than or equal to 0.2%.

Furthermore, in one embodiment, the process of the invention can comprise a stage of extraction of the organometallic complex and of the organophosphorus ligands from the medium comprising the nitrites and in particular the dinitriles by liquid/liquid extraction using an extraction solvent. Mention may be made, as suitable extraction solvent, by way of examples, of saturated, linear or cyclic, aliphatic hydrocarbons, such as hexane, heptane, octane, cyclohexane, cyclopentane, cycloheptane and more generally cycloparaffins or analogues. Cyclohexane is the preferred extraction solvent.

The solution of ligands and of organometallic complex in the extraction solvent is also subjected to distillation in order to separate the extraction solvent and to recycle the ligands and the organometallic complex thus recovered. In the present invention, the extraction solvent is a reactant used for the implementation of the process.

This separation is also carried out while observing the characteristics of the invention indicated above, such as ligand/nickel ratio, concentration of nickel and distillation bottom temperature.

According to a preferred embodiment of the invention, this separation of the cyclohexane is carried out with a distillation bottom temperature of less than or equal to 180° C. for a concentration by weight of nickel of greater than or equal to 0.7%. In addition, according to a preferred characteristic of the invention, the ratio of moles of bidentate ligand, expressed as phosphorus atoms, to the number of nickel atoms is between 1 and 4 (limits included) and that of the monodentate ligand is greater than or equal to 8.

According to the invention, in the stages of separation by distillation starting from a medium comprising the catalytic system, the maximum temperature of the distillation bottoms is determined and is a function of the ligand/nickel ratio and of the concentration of nickel in the medium. Thus, this temperature increases as the ligand/nickel ratio increases and/or as the concentration of nickel increases.

In a preferred embodiment of the invention, the process comprises a stage of separation of the catalytic system and of the dinitriles carried out in a stage of settling into two dense and light phases. The medium fed to this settling stage is either the medium obtained after the second hydrocyanation stage or the distillation bottoms obtained in the stage of separation of the unreacted unsaturated nitrites.

Thus, the lower or dense phase comprises most of the nickel and of the bidentate ligand and a portion of the monodentate ligand, the upper or light phase being composed of the dinitriles and the remaining portion of the nickel and of the mono- and bidentate ligands.

The medium fed to the settling stage is advantageously cooled to a temperature of between 25 and 75° C., preferably between 30 and 55° C.

According to another characteristic of the process of the invention, the upper phase recovered in the settling stage comprises a ligand/nickel molar ratio advantageously of greater than 8.

According to the invention, the total recovery of the metal complex and of the ligands is carried out by liquid/liquid extraction of these using an extraction solvent which is immiscible with the dinitriles. This operation corresponds to that described above, the solvents being identical.

In this embodiment, it is advantageous, prior to the stage of distillation of the unreacted unsaturated nitrites, to adjust and to control the concentration of nickel in the medium by addition of a portion of the lower or dense phase recovered in the settling stage.

This is because the concentration of nickel used in the hydrocyanation medium, when the nickel is used in combination with a bidentate ligand in accordance with the process of the invention, can be very low, such as, for example, of the order of 100 to 2000 mg of nickel/kg of reaction medium. In order to obtain a concentration of nickel suitable for promoting the settling, it may be necessary to add a certain amount of catalytic system to the reaction medium exiting from the hydrocyanation stage. This adjustment to the concentration of nickel can be made as indicated above.

The process of the invention thus makes possible recovery and separation of the catalyst with a loss of metal element and thus of catalyst which is minimized.

The present invention preferably applies to the hydrocyanation of butadiene and of linear or branched unsaturated nitrites comprising from 3 to 8 carbon atoms and more preferably of 3-pentenenitrile and/or 4-pentenenitrile for the production of adiponitrile with use of a catalyst of the type represented by the following formula:

$$Ni(L_1)_x(L_2)_y$$

in which $L_1$ represents a monodentate ligand and $L_2$ a bidentate ligand, x and y represent decimal numbers ranging from 0 to 4, the sum x⊕2y being equal to 3 or 4.

The catalyst can be composed of a mixture of complexes corresponding to the above general formula.

The catalytic system or the reaction medium can also comprise an amount of mono- and/or bidentate organophosphorus ligand in the free form, that is to say not bonded to the nickel. The catalytic systems of the invention can be obtained by formation, in a first stage, of an organometallic complex between the nickel and monodentate ligand. Processes for the formation of such complexes are, for example, disclosed in patents U.S. Pat. Nos. 3,903,120 and 4,416,825.

In a second stage, the bidentate ligand is added to the medium comprising the said organometallic complex.

The first and second hydrocyanation stages are advantageously carried out in series. In this case, it is advantageous for at least a portion of the catalyst recovered, in particular that recovered in the liquid/liquid extraction, and more particularly the catalyst recovered in the upper phase of the settling stage, to be recycled and used as catalyst in the first stage of hydrocyanation of butadiene and/or in the stage of isomerization of branched unsaturated nitriles to linear unsaturated nitriles. The use of an identical or similar catalytic system for the hydrocyanation of butadiene and that of pentenenitriles is preferred.

However, it is also possible to use the catalytic system described above solely in the stage of hydrocyanation of unsaturated nitriles, the catalytic system used in the first stage of hydrocyanation of butadiene and the isomerization stage being different, in the nature of the compounds.

Other details and advantages of the invention will become more clearly apparent in the light of the examples given below solely by way of illustration.

Abbreviations Used in the Examples:
PN: pentenenitriles
DN: dinitriles (mixture of dinitriles AdN, MGN and ESN, predominantly comprising AdN)
AdN: adiponitrile
MGN: methylglutaronitrile
ESN: ethylsuccinonitrile
Ligands:

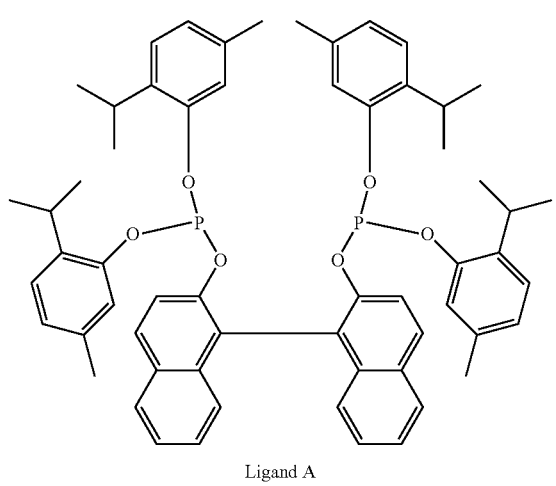

Ligand A

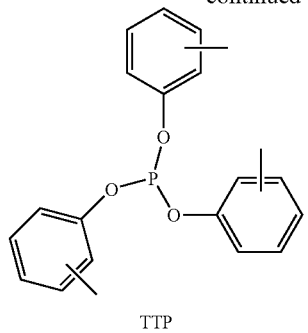

TTP

EXAMPLE 1

Distillation of the Pentenenitriles (PN)

A mixture with the following composition is prepared under an inert atmosphere (the percentages are expressed by weight; the ratios are molar ratios):
Ni=1.2%
TTP/Ni=5
Ligand A/Ni=1
P/Ni=7
DN=38.5%
PN=5%

This mixture is introduced into a tube, which is sealed and heated at a certain temperature (see Table) for 2 h, then the loss of complexed nickel is determined by chromatographic analysis:

| Temperature | Loss of Ni |
|---|---|
| 130° C. | 0% |
| 150° C. | 25% |

EXAMPLE 2

Stage of Distillation of the Solution Obtained after Liquid/Liquid Extraction

A mixture with the following composition is prepared under an inert atmosphere (the percentages are expressed by weight; the ratios are molar ratios):
Ni=1.0%
TTP/Ni=12
Ligand A/Ni=1
P/Ni=13
PN=11%

This mixture is introduced into a tube, which is sealed and heated at a certain temperature (see Table) for 2 h, and the loss of complexed nickel is determined by chromatographic analysis:

| Temperature | Loss of Ni |
|---|---|
| 170° C. | 0% |
| 190° C. | 45% |

The invention claimed is:

1. A process for the hydrocyanation of unsaturated compounds, the process comprising:
   (a) hydrocyanating an unsaturated compound using at least one stage of hydrocyanation, wherein the hydrocyanation is performed in the presence of a catalytic system comprising an organometallic complex formed by one or more organophosphorus ligands of monodentate organophosphite and one or more bidentate organophosphorus ligands, and optionally a Lewis acid promoter, wherein a reaction medium comprising a reactant and a compound formed by the reaction is formed and
   (b) separating a reactant or a compound formed by the hydrocyanation reaction from the reaction medium using at least one stage of separation by distillation of a reactant used in the process or of a compound formed by the reaction from a medium comprising said catalytic system, wherein the reaction medium subjected to the stage of separation by distillation comprises a ratio of the number of moles of organophosphorus ligands, expressed as phosphorus atoms, with respect to the number of metal element atoms of less than or equal to 15 and/or a concentration by weight of metal element forming the organometallic complex of less than or equal to 1.3%, and the distillation bottom temperature of the distillation stage being less than or equal to 180° C.

wherein the one or more organorhosphorus ligands of monodentate organophosphite is triphenyl phosphite, tritolyl phosphite or tricymenyl phosphite, wherein the unsaturated compound is butadiene and/or an unsaturated nitrile compound, and wherein the bidentate organophosphorus ligand is one of the compounds with the following structures, wherein Ph means phenyl:

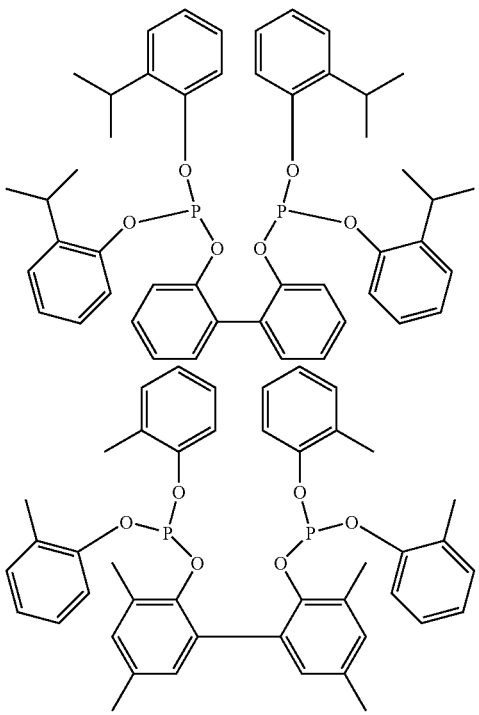

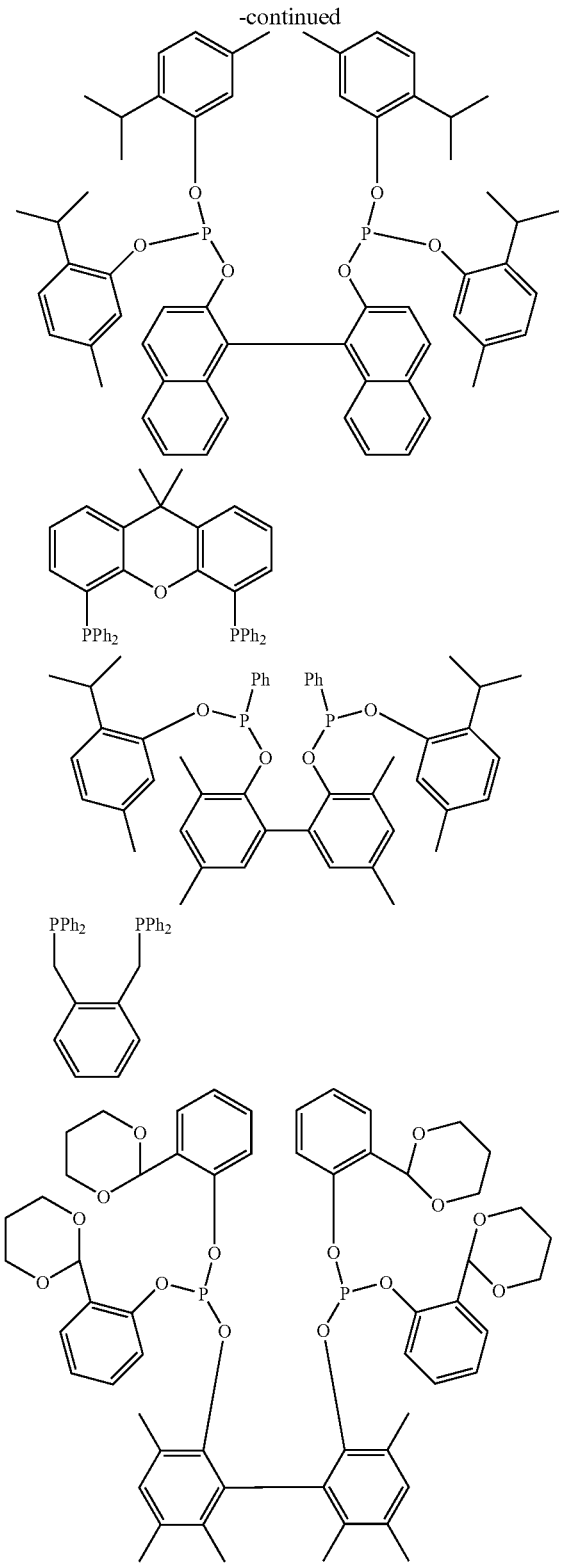

2. The process according to claim 1, wherein the Lewis acid promoter is selected from the group consisting of halides, sulphates, sulphonates, haloalkylsulphonates, perhaloalkylsulphonates, haloacetates, perhaloacetates, carboxylates, phosphates, arylboranes, fluoroalkylsulphonates and perfluoroalkylsulphonates of elements from Groups Ib, IIb, IIIa, IIIb, IVa, IVb, Va, Vb, VIIb, VIIb or VIII of the Periodic Table of the Elements.

3. The process according to claim 2, wherein the Lewis acid promoter is selected from the group consisting of zinc chloride, zinc bromide, zinc iodide, manganese chloride, manganese bromide, cadmium chloride, cadmium bromide, stannous chloride, stannous bromide, stannous sulphate, stannous tartrate, indium chloride, indium trifluoromethylsuiphonate, indium trifluoroacetate, chlorides of rare earth elements, bromides of rare earth elements, cobalt chloride, ferrous chloride, yttrium chloride, triphenylborane, and titanium tetraisopropoxide.

4. The process according to claim 1, wherein the unsaturated compound is a linear or branched nitrile having from 3 to 8 carbon atoms.

5. The process according to claim 4, wherein the unsaturated nitrile is a pentenenitrile.

6. The process according to claim 1, wherein the stage of separation by distillation separates the unreacted unsaturated compound from the reaction medium.

7. The process according to claim 1, further comprising recovering the catalytic system by settling the reaction medium resulting from the hydrocyanation of an unsaturated nitrile, optionally after separation by distillation of the unreacted unsaturated nitrile.

8. The process according to claim 6, further comprising the step of extracting the organophosphorus ligands and the organometallic complex from the reaction medium resulting from the hydrocyanation of an unsaturated nitrile, by liquid/liquid extraction, wherein the step of extracting the organophosphorus ligands and the organometallic complex is optionally performed after separating unreacted mononitrile from the reaction mixture or after performing a settling stage, where an upper and lower phase are formed and the upper phase is extracted.

9. The process according to claim 8, wherein the extraction solvent is hexane, heptane, octane, cyclohexane, cyclopentane or cycloheptane.

10. The process according to claim 6, wherein the separation stage is a stage of distillation of the extraction solvent from the solution obtained after liquid/liquid extraction.

11. The process according to claim 6, further comprising performing a settling stage where an upper and lower phase are formed, wherein a portion of said lower phase is recycled in the reaction medium resulting from the hydrocyanation, before the stage of distillation of the unsaturated nitrites.

* * * * *